United States Patent [19]

Runge

[11] 4,143,425
[45] Mar. 13, 1979

[54] LEFT ATRIAL TO DESCENDING THORACIC AORTA LEFT VENTRICULAR ASSIST DEVICE

[76] Inventor: Thomas M. Runge, 2501 Galewood Pl., Austin, Tex. 78703

[21] Appl. No.: 846,109

[22] Filed: Oct. 27, 1977

[51] Int. Cl.² .......................... A61F 1/24; A61M 1/03
[52] U.S. Cl. ........................................ 3/1.7; 128/1 D; 92/31; 74/57; 417/412
[58] Field of Search ............ 3/1.7; 128/1 D, DIG. 3; 74/57; 92/31; 417/412

[56] References Cited

U.S. PATENT DOCUMENTS

| | | | |
|---|---|---|---|
| 1,921,235 | 8/1933 | Lindsey | 74/57 |
| 2,245,457 | 6/1941 | Brassell | 74/57 |
| 2,361,821 | 10/1944 | Crowe et al. | 74/57 |
| 2,917,751 | 12/1959 | Fry et al. | 3/1.7 |
| 3,518,033 | 6/1970 | Anderson | 3/1.7 |
| 3,791,769 | 2/1974 | Kovacs | 3/1.7 X |
| 3,860,968 | 1/1975 | Shapiro | 3/1.7 |
| 3,911,898 | 10/1975 | Leachman, Jr. | 3/1.7 X |

Primary Examiner—Ronald L. Frinks
Attorney, Agent, or Firm—B. P. Fishburne, Jr.

[57] ABSTRACT

An implanted tether-free externally powered motor with suitable reduction gearing drives a spirally grooved shaft having a ring housing for a shaft follower pin. A rectangular cross section chamber receives an ejection plate pivoted near one end to a first leg of the ring housing and having a resilient lost motion connection with a second leg of the ring housing near its other end. A compressible sac or pouch extends through said chamber and is fitted at its opposite ends with porcine valves and has conduit extensions outwardly of said valves for connection with the left atrium and the descending thoracic aorta, respectively. During use, the sac or pouch is cyclically compressed by the ejection plate, initially at the end of the ejection plate having the lost motion yielding connection with the follower ring housing, and subsequently at both ends of the ejection plate so that a predetermined volume of blood is delivered on each stroke of the ejection plate to the thoracic aorta.

10 Claims, 6 Drawing Figures

LEFT ATRIAL TO DESCENDING THORACIC AORTA LEFT VENTRICULAR ASSIST DEVICE

CROSS-REFERENCE TO RELATED APPLICATION

This application contains subject matter in common with application Ser. Number 760,322, filed Jan. 18, 1977, for CARDIAC PUMPING DEVICE, now U.S. Pat. No. 4,058,855.

BACKGROUND OF THE INVENTION

The above-referenced patent application and prior U.S. Pat. No. 4,004,299 both disclose cardiac pumping devices in which the rotation of a spiral driver produces linear movement of a follower assembly which, during movement in one direction, compresses two blood compatible sacs which simulate the left ventricle and right ventricle of the heart by pumping blood through the aorta and pulmonary artery, respectively. In the prior art devices, return movement of the follower assembly in terms of rate is a function of right atrial and left atrial pressure and volume. Stroke volume of each simulated ventricle is independent of the other as in the natural heart. In the device of the pending application above-referenced, the mechanism automatically adjusts its rate of pumping in accordance with both preload (filling pressure) and afterload (pulmonic and systemic pressure), and in addition modifies its stroke volume in a downward direction when confronted with high afterload. This automatic adjustment of the device during operation depends on several variables and is accomplished without electronic control or monitoring.

The present invention, while possessing all of the attributes of the above two prior art devices, is a special adaptation thereof to provide a left atrial to descending thoracic aorta left ventricle assist device. In achieving this objective, the basic drive means of the prior patent and pending application are utilized in conjunction with a thin walled rectangular cross-section compression chamber for a Dacron pouch which extends through the chamber and is equipped beyond the ends of the chamber with a pair of porcine valves and conduit extensions which are connected to the left atrium and the descending thoracic aorta, respectively.

Within the compression chamber is a flat rectangular ejection plate having a pivot lug near the lower or aortic end thereof for pivotal connection with one drive leg of a follower ring housing which surrounds the spiral drive shaft or element. Near its upper or left atrial end, the ejection plate carries a laterally projecting pivoted extension pin equipped at its free end with a spring. The extension pin and spring are received in a tubular leg of the follower ring housing and the spring can bottom in this leg. In response to linear displacement of the ring follower housing, the end of the ejection plate proximal to the left atrium is first forced into compressive engagement with the Dacron pouch by the action of the extension pin-spring connection with said tubular leg. Subsequently, during further movement of the ring follower housing, both ends of the ejection plate are equally and fully moved into compressive engagement with the Dacron pouch to force a predetermined volume of blood from the left atrium to the pouch and into the descending thoracic aorta.

Other features and advantages of the invention will become apparent during the course of the following description.

DETAILED DESCRIPTION

Figure 1:
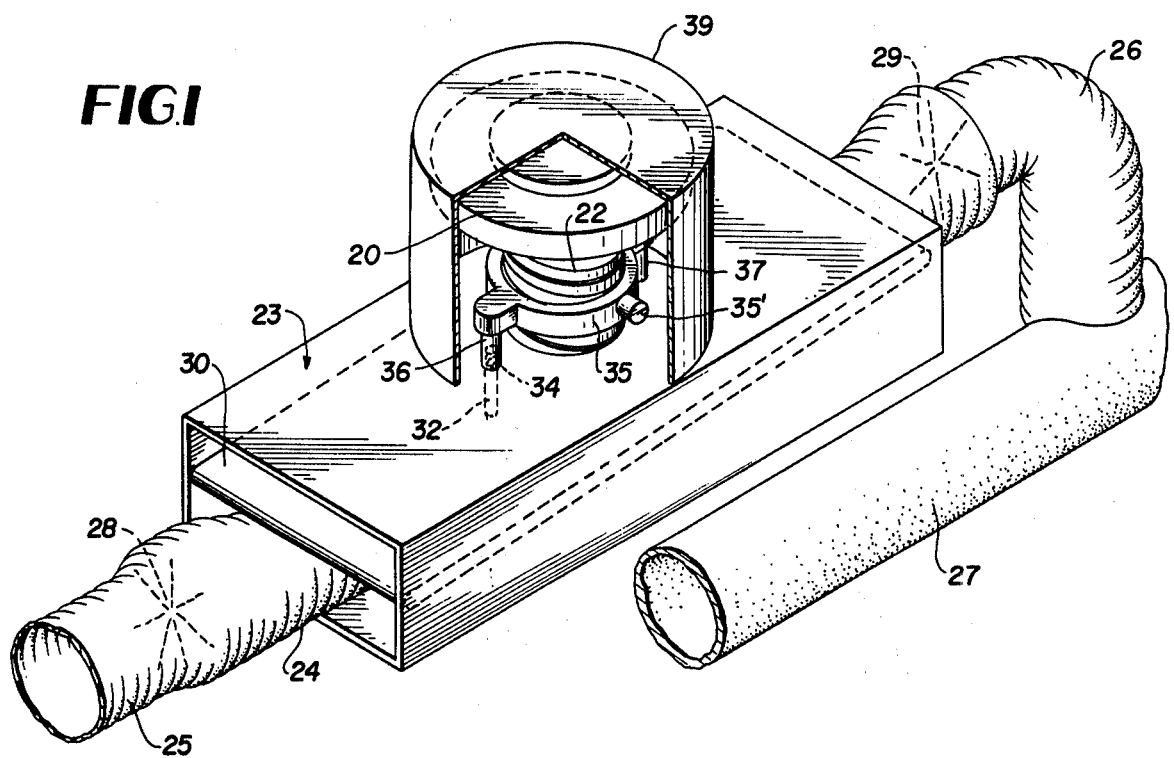
FIG. 1 is a partly schematic perspective view of the invention.

Referring to the drawings in detail and initially to FIGS. 1 through 4, wherein like numerals designate like parts, the numeral 20 designates a pancake drive motor having suitable built-in reduction gearing, and adapted to be powered across intact skin of a host without external connections, as explained in the referenced prior art devices. An output shaft 21 of pancake motor 20 is operatively connected with a spirally grooved rotary shaft 22 having one end bearing on the top wall of a rectangular cross section metal compression chamber 23, as indicated at 23'. The motor 20 and grooved shaft 22 may be identical to the corresponding elements disclosed in referenced U.S. Pat. No. 4,004,299.

The rectangular compression chamber 23 is open ended and receives therethrough lengthwise a preferably Dacron compressible sac or pouch 24 having end conduit extensions 25 and 26 for connection, respectively, to the left atrium, not shown, and to the descending thoracic aorta 27 shown schematically in FIG. 1. Beyond the ends of the compression chamber 23, the pouch 24 is equipped with proximal and distal porcine valves 28 and 29, FIG. 3, which guard the orifices of the pouch 24.

Within the compression chamber 23 on one side of the pouch 24 is a flat rectangular ejection plate 30 extending substantially for the length and width of the chamber 23, and provided at its end nearest the extension 26 with an apertured pivot lug 31, and similarly provided near its other end with a laterally extending pin or rod 32, pivotally attached at 33 to the ejection plate 30. The end of the rod away from the ejection plate 30, FIG. 2, carries a compression spring 34 whose purpose will be described.

Surrounding the grooved rotary shaft 22 is a ring follower housing 35 having a tubular leg 36 and a solid leg 37 rigidly connected therewith and projecting from one side thereof axially of the grooved shaft 22. The legs 36 and 37 are spaced apart diametrically of the shaft 22 on opposite sides thereof. The spacing of the legs 36 and 37 enables them to be coupled with the ejection plate 30 in the following manner. The pivoted rod 32 is received telescopically and slidably in the tubular leg 36 along with the spring 34. The solid leg 37 of the ring housing 35 is connected pivotally at 38 with the previously-described lug 31 of the ejection plate.

Figure 2:
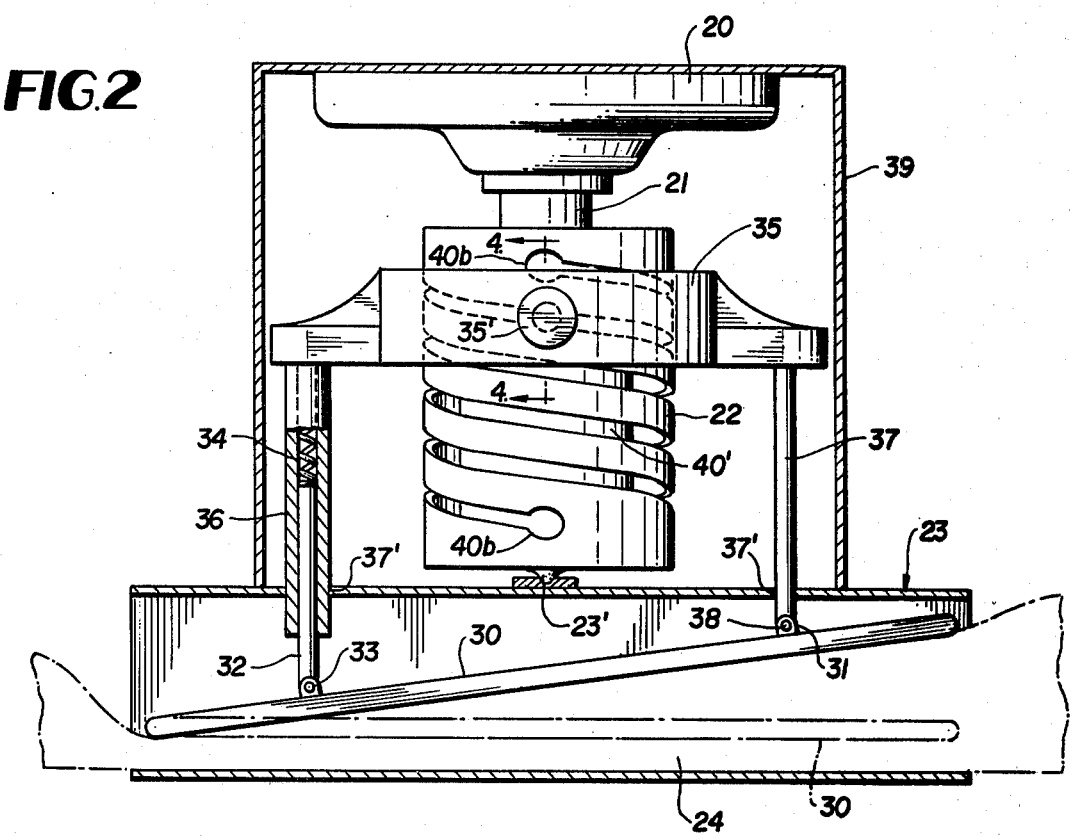
FIG. 2 is an enlarged central vertical section, partly in elevation, taken through the invention in FIG. 1.

A housing or shell 39 encloses the motor 20, drive shaft 32 and ring housing 35 with the open end of the shell remote from the motor seated on one wall of the compression chamber 23, as illustrated. The shell 39 is fixed to the chamber 23 in any conventional manner. As best shown in FIG. 2, the legs 36 and 37 project slidably through openings 37' in the chamber 23 into the interior of the chamber for connection with the pin 32 and lug 31 in the described manner near the pouch 24.

Figure 4:
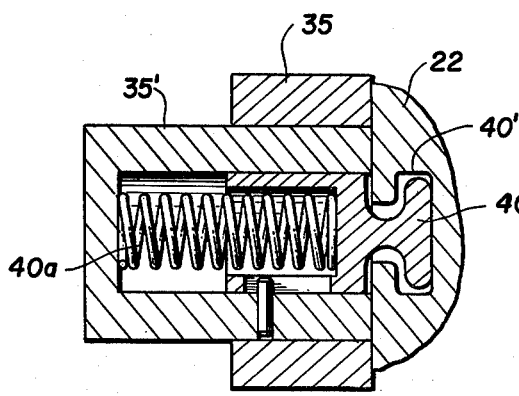
FIG. 4 is an enlarged fragmentary vertical section taken on line 4—4 of FIG. 2.
Figure 3:
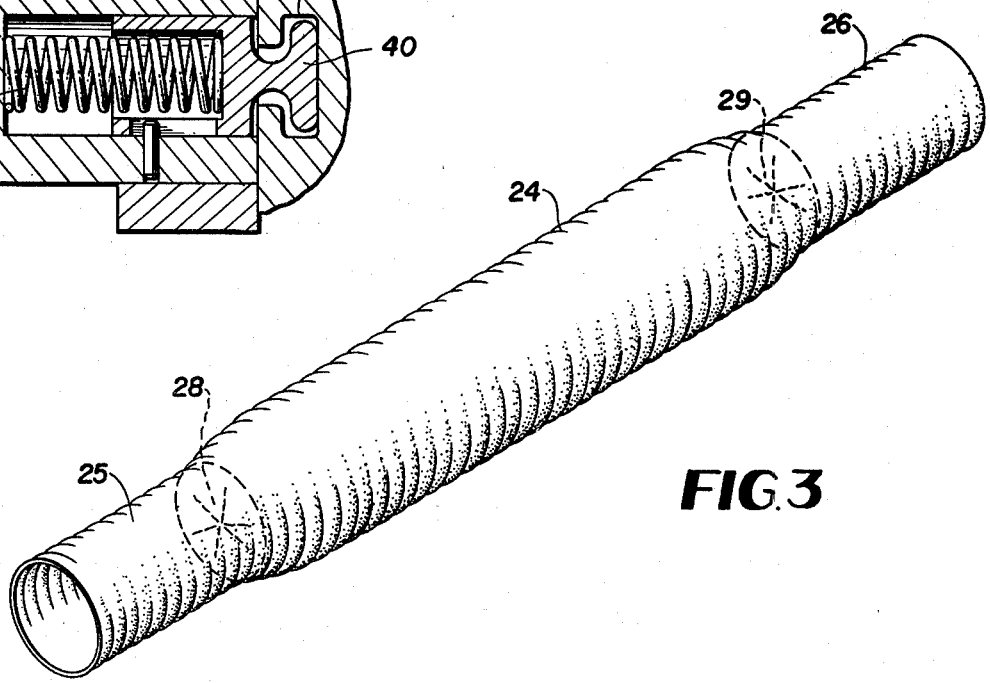
FIG. 3 is a perspective view of a compressible sac or pouch and associated valves employed in the invention.

The ring housing 35 carries a radial housing 35' rigid therewith and this housing contains a follower pin 40, FIG. 4, whose head engages in and follows the groove 40' of rotary shaft 22 exactly as disclosed in U.S. Pat. No. 4,004,299. The follower pin 40 is urged forwardly by a spring 40a in the housing 35 as disclosed in said patent. No further description of the follower pin is required, as the disclosure of said patent is incorporated herein by reference.

The two legs 36 and 37 travel with the ring housing 35 as the latter reciprocates axially of the rotating grooved shaft 22 due to the coaction of the follower pin 40 with the spiral groove 40' and its entrance and exit recesses 40b near opposite ends of the shaft 22. As the ring housing 35 is advanced cyclically toward the compression chamber 23 during rotation of the shaft 22 to cause compression of the pouch 24 by ejection plate 30, the tension of spring 34 bottoming in the tubular leg 36 will be sufficient to maintain the pin 32 extended and the ejection plate 30 inclined approximately as shown in FIG. 2. As a result of this, the end portion of the pouch 24 nearest the left atrium, or to the left in FIG. 2, will be compressed initially by the plate 30 while the other end portion of the pouch nearest the thoracic aorta remains comparatively uncompressed. However, as the ring housing 35 travels further on the grooved shaft toward the chamber 23, the spring 34 will gradually yield and the rod 32 will move further into the bore of leg 36, while the rigid leg 37 simultaneously is moving the adjacent end of ejection plate 30 into greater compressive relationship with pouch 24. Eventually, as the movement of the ring housing 35 continues toward the chamber 23, the ejection plate 30 will lie parallel to the main side walls of the chamber 23 as shown in broken lines in FIG. 2. When this condition prevails, the pouch 24 will be substantially completely compressed at both ends of the ejection plate 30 and the blood will be expelled from the pouch in the direction of the extension 26 leading to the descending thoracic aorta. This unique mode of operation enables a predetermined volume of blood in the pouch 24 admitted through the valve 28 to be expelled through the valve 29 during each positive displacement of the ring housing 35 axially on the grooved shaft 22 in one direction. The return stroke of the ring housing 35 on the shaft 22 takes place through coaction of the follower pin 40 with the shaft as described in the above-referenced patent.

Figure 5:
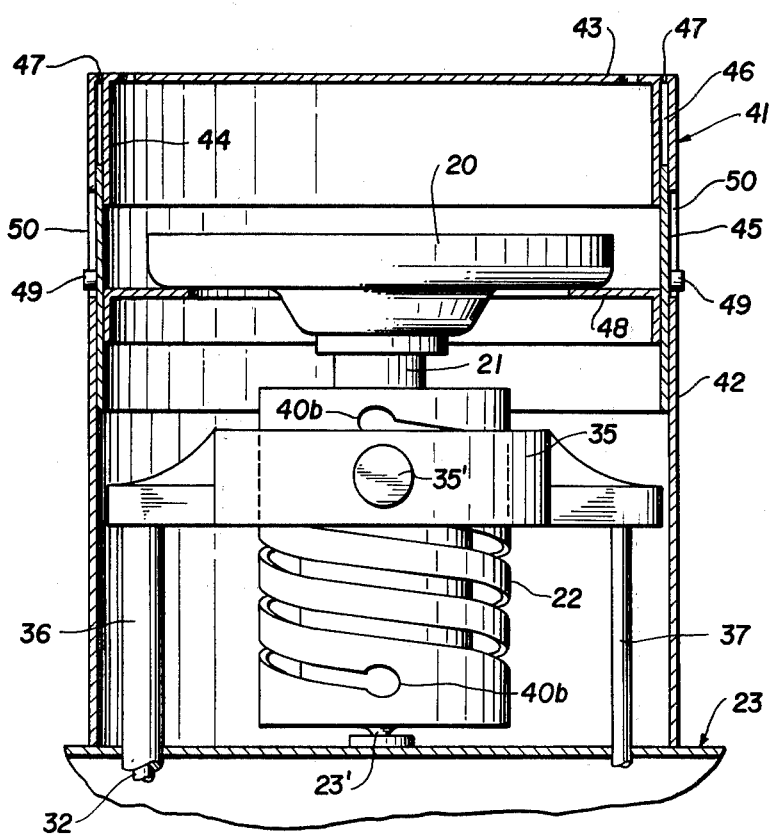
FIG. 5 is a cross sectional view, similar to FIG. 2, showing an additional capability of the invention in accordance with a variant thereof.

An additional feature of the invention not shown in FIGS. 1 and 2 is disclosed in FIG. 5, and it is preferable to incorporate this feature in the invention. In lieu of the simple one-piece shell 39, a modified shell 41 has its main side wall 42 resting on and fixed to the chamber 23 similar to the shell 39. The top wall 43 of shell 41, however, has an interior wall section or sleeve 44 depending therefrom in spaced relation to the outer wall 42 for a considerable distance. An intermediate sleeve member 45 is mounted for reciprocation relative to the spaced walls 42 and 44 in the space 46 between these walls, the end of this space being vented as at 47 by a number of small vent apertures. The pancake motor 20 is seated on and secured to an internal ring member 48 fixed to the interior of the movable sleeve member 45. The motor and sleeve member 45 are held against rotation by a pair of pins 49 projecting from the sleeve member 45 and being received in guide slots 50 of the outer wall 42, which slots are straight and parallel to the axis of the shaft 22. The arrangement permits the pancake motor 20 and all parts coupled therewith to shift axially at proper times relative to the shell or casing 41 which is rigidly attached to compression chamber 23.

Again referring to U.S. Pat. No. 4,004,299 and application Ser. No. 760,322, the arrangement described immediately above in connection with FIG. 5 allows the invention to increase its stroke volume when confronted with low afterload, or conversely, decrease its stroke volume when confronted with high afterload. This is an important added capability. The mechanism in FIG. 5 also possesses increased resistance to jamming. By virtue of the arrangement in FIG. 5, when the ejection plate 30 is confronted with high pressure or resistance, the sleeve member 45 to which the motor 20 is fixed can move away from the compression chamber 23 and slide into the space 46 which is vented at 47. The degree of movement or "sink" into this space is time dependent as well as pressure dependent. Consequently, the present invention maintains the capability of increasing or decreasing its stroke volume with low or high afterload in accordance with the referenced patent and application.

During each operating cycle of the ejection plate 30 on the pouch 24, more than 50 cc of blood can be forced by the device into the descending thoracic aorta 27 during the patient's cardiac diastole. Such pumping may be synchronized to the QRS complex by state-of-the art techniques. At a pumping rate of 60 perminute, not less than 3000 cc of blood per minute can be added by the invention to the patient's cardiac output, or enough to sustain life when there is zero output from the patient's left ventricle. The device of the invention can also be used for right atrial to pulmonic artery implantation or right ventricular assistance. The device can be inserted in a relatively simple operation in seriously ill patients and removed surgically when it is no longer needed.

Figure 6:
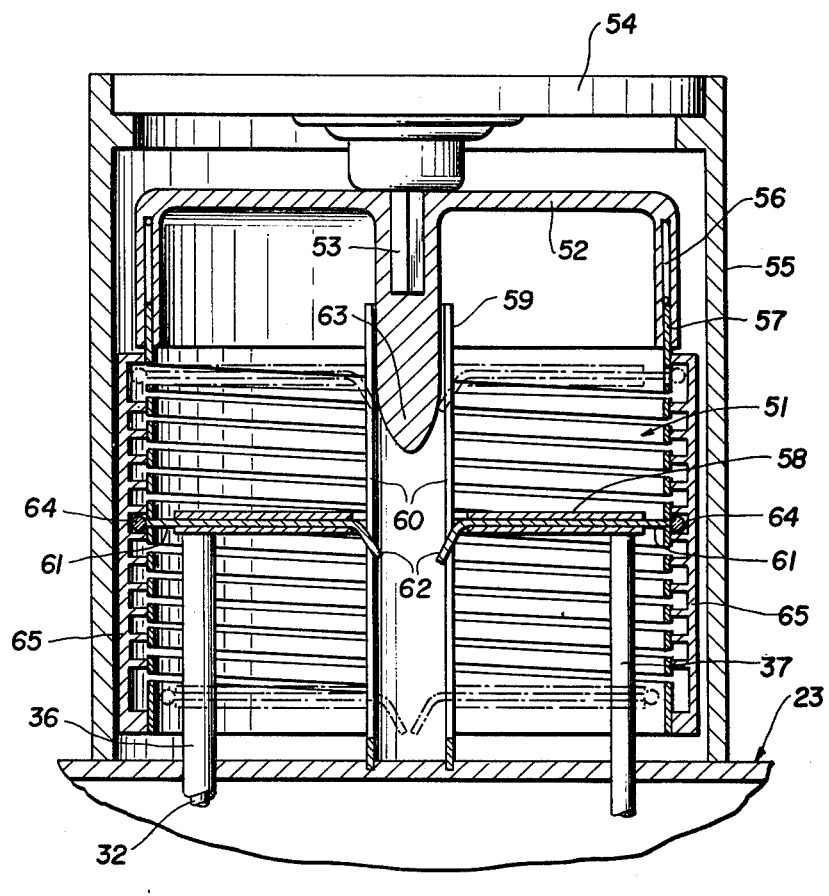
FIG. 6 is another cross sectional view taken through the invention according to a modification thereof.

FIG. 6 of the drawings shows a modification in which the rotary drive means of referenced application Ser. No. 760,322 is adapted to the invention without altering in any way the general mode of operation of the invention embodied in the compression chamber 23, ejector plate 30 and the associated elements 36, 37 and 32, etc. In lieu of the grooved shaft 22, the manufacturing of which is somewhat costly, a wider diameter spirally slitted rotary drive sleeve 51 identical to the drive sleeve in said application is employed. The sleeve is coupled and driven rotationally by a drive cup 52 at one end thereof, the cup being coupled with the output shaft 53 of a pancake motor 54 held within a housing 55, one end of which abuts and is suitably fixed to the compression chamber 23. The drive cup 52 may contain a light sinusoidal spring 56 within an annular slot formed in the side wall of the cup, the slot also receiving an end skirt portion 57 of the slitted sleeve 51, as described in said application and for the purposes set forth therein.

The device in FIG. 6 further comprises a flat annular disc 58 which surrounds a stationary central guide tube 59 having side longitudinal slots 60 formed therein. The disc 58 is spanned diametrically by a pair of drive arms 61 which are held in radial passages of the disc slidably so that the arms may shift radially inwardly and outwardly at certain times during the operation of the mechanism. At their inner ends, the drive arms 61 carry inclined cam extensions 62 for engagement with a bullet-like cam 63 carried by the cup 52. At their outer ends, the drive arms 61 carry ball heads 64. These ball heads engage toothed longitudinal stabilizing bars 65 outwardly of the thin slitted sleeve 51 and the ball heads cannot pass through the narrow spiral slit of the sleeve 51. The construction and operation of the drive mechanism in FIG. 6 is fully disclosed in said referenced application, and therefore need not be further described herein for a full understanding of the invention.

In lieu of the ventricular sacs 52 and 53 in said application, which are cyclically compressed by reciprocation of the disc, the corresponding disc 58 in FIG. 6 is attached directly to the legs 36 and 37 of the present invention, as shown, and drives these legs in the same manner that they are driven by the ring housing 35 of the preceding embodiment. The functioning of the modified drive mechanism in relation to the chamber 23, ejection plate 30, and the compressible pouch 24 is exactly as previously described and need not be repeated. Also, the two disclosed drive mechanisms involving shaft 22 and follower pin 40, and slitted sleeve 51 with drive arms 61 operate precisely as described in said patent and application and therefore do not require a more detailed description herein for a full understanding of the invention.

The invention is characterized by reliability in operation, simplicity in construction and comparative economy of manufacturing. Its utility should be readily apparent to those skilled in the art.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. A cardiac assist device comprising a substantially rigid compression chamber having opposite end openings, a compressible pouch extending longitudinally through said compression chamber and adapted for connection outside of said chamber with cardiac circulatory elements, check valve means in opposite end portions of said pouch, an ejection plate in said compression chamber on one side of the pouch, and a power drive means connected with said ejection plate including a pair of drive elements spaced longitudinally on the ejection plate and pivoted thereto, and means forming a yielding connection in the power drive means with one of said drive elements whereby in the operation of the device the pouch is compressed by the ejection plate first at one end portion of the pouch and subsequently at the opposite end portion so that predetermined volumes of blood are expelled cyclically from the pouch at its end which is compressed last by the ejection plate.

2. A cardiac assist device as defined in claim 1, and said power drive means including rotational means and linear reciprocatory drive means operationally coupled with the rotational means and including said pair of longitudinally spaced drive elements pivoted to the ejection plate.

3. A cardiac assist device as defined in claim 2, in which said rotational means comprises a motor, a spirally grooved shaft coupled with and driven by the motor, and a follower pin element engageable in the spiral groove of the shaft and being attached to and driving said linear reciprocatory drive means.

4. A cardiac assist device as defined in claim 2, in which said rotational means comprises a motor, a spirally slitted sleeve coupled with and driven by the motor, and a follower disc means engaged with the spiral slit of said sleeve and attached to and forming a part of said linear reciprocatory drive means.

5. A cardiac assist device as defined in claim 2, and one of said longitudinally spaced drive elements comprising a rigid leg having a pivotal connection with said ejection plate near one end thereof, and a telescoping leg having one component pivotally connected with the ejection plate near the other end thereof, and a spring interposed between the telescoping components of said telescoping leg.

6. A cardiac assist device as defined in claim 1, in which said pouch is adapted for connection at its end which is first compressed by the ejection plate with the left atrium of the heart and at its other end which is lastly compressed by the ejection plate with the descending thoracic aorta to thereby form a left ventricular assist means.

7. A cardiac assist device as defined in claim 2, and said linear reciprocatory drive means comprising a follower ring housing surrounding and coupled with and driven by said rotational means, and said pair of longitudinally spaced drive elements being carried by said follower ring housing on diametrically opposite sides of the rotational drive means, the rotational drive means including a motor adapted to be energized from means external to the host without external connections.

8. A cardiac assist device as defined in claim 7, and one of said longitudinally spaced drive elements being a rigid leg on said follower ring housing pivoted to the ejection plate near the end thereof which is last moved into compressive relationship with the pouch, and a telescoping leg having resistive spring means and pivotally connected with the ejection plate near the end thereof which first compresses the pouch.

9. A cardiac assist device as defined in claim 1, and said compression chamber comprising an elongated section of rectangular cross section tubing, and said ejection plate comprising a unitary flat plate within said tubing section and being approximately coextensive in length and width therewith.

10. A cardiac assist device as defined in claim 9, and said pouch formed from an elongated fabric tubing section and having end terminals extending beyond opposite ends of the compression chamber and beyond said check valve means, whereby the end terminals of the pouch may be attached to said cardiac circulatory elements in a host receiving the device.

* * * * *